United States Patent
Götz

(10) Patent No.: US 12,232,965 B2
(45) Date of Patent: Feb. 25, 2025

(54) PATIENT SPECIFIC GRAFT CAGE FOR CRANIOMAXILLOFACIAL REPAIR

(71) Applicant: DePuy Synthes Products, Inc., Raynham, MA (US)

(72) Inventor: Mario Götz, Bretten (DE)

(73) Assignee: DePuy Synthes Products, Inc., Raynham, MA (US)

(*) Notice: Subject to any disclaimer, the term of this patent is extended or adjusted under 35 U.S.C. 154(b) by 600 days.

(21) Appl. No.: 17/386,805

(22) Filed: Jul. 28, 2021

(65) Prior Publication Data
US 2022/0031460 A1    Feb. 3, 2022

Related U.S. Application Data

(60) Provisional application No. 63/057,913, filed on Jul. 29, 2020.

(51) Int. Cl.
*A61F 2/30* (2006.01)
*A61F 2/28* (2006.01)

(52) U.S. Cl.
CPC ........ *A61F 2/30942* (2013.01); *A61F 2/2875* (2013.01); *A61F 2002/2878* (2013.01);
(Continued)

(58) Field of Classification Search
CPC ............ A61F 2002/2878; A61F 2/2875; A61F 2/30942; A61F 2002/30943; A61F 2002/30948
See application file for complete search history.

(56) References Cited

U.S. PATENT DOCUMENTS 5,139,497 A * 8/1992 Tilghman .............. A61F 2/2875
606/70
5,380,328 A    1/1995 Morgan
(Continued)

FOREIGN PATENT DOCUMENTS

DE    102015118318 A1    4/2017
KR    20190140720 A  * 12/2019
(Continued)

OTHER PUBLICATIONS

Cho et al., Intrinsically reversible superglues via shape adaptation inspired by snail epiphragm. Proceedings of the National Academy of Sciences of the United States of America. vol. 116, Jul. 9, 2019, p. 13774-13779.
(Continued)

*Primary Examiner* — Javier G Blanco
(74) *Attorney, Agent, or Firm* — BakerHostetler

(57) ABSTRACT

A method of forming a patient-specific-bone-graft cage based on a patient-specific bone graft cage computer model that is based on a contour of a surface of the bone defining a void, and/or a patient-specific-bone-graft cage that includes a plurality of apertures, that terminate at a location between a front surface and a back surface of the patient-specific-bone-graft cage, for receipt of bone graft material. The patient-specific-bone-graft cage can construct an essential portion (including complex thin anatomical structures) of or substantially the entirety of the mid-face region (e.g., to fill a void in a damaged orbital region), which enables an improved structure reproduction and simplification for the surgeon. For example, the patient-specific-bone-graft cage may be formed based on the contour of the periphery defining the void in the damaged region, and require less modification by a surgeon compared to graft cages formed only by mirroring techniques or normalized models.

12 Claims, 9 Drawing Sheets

(52) U.S. Cl.
CPC .............. *A61F 2002/30062* (2013.01); *A61F 2002/30943* (2013.01); *A61F 2002/30948* (2013.01); *A61F 2002/30985* (2013.01)

(56) References Cited

U.S. PATENT DOCUMENTS

| | | |
|---|---|---|
| 7,662,155 B2 | 2/2010 | Metzger et al. |
| 8,313,517 B2 | 11/2012 | Mohr et al. |
| 2004/0054372 A1 | 3/2004 | Corden et al. |
| 2006/0224242 A1 | 10/2006 | Swords et al. |
| 2010/0192661 A1* | 8/2010 | Metzger ................ B21D 35/00 72/457 |
| 2014/0003695 A1 | 1/2014 | Dean et al. |
| 2015/0105858 A1* | 4/2015 | Papay .................... A61L 27/18 623/11.11 |
| 2015/0328004 A1* | 11/2015 | Mafhouz ................ G06F 30/00 700/98 |
| 2016/0287391 A1 | 10/2016 | Arsen et al. |
| 2018/0271661 A1* | 9/2018 | Kamer .................. A61F 2/2875 |
| 2018/0318011 A1 | 11/2018 | Leibinger et al. |
| 2019/0231531 A1 | 8/2019 | Gordon |

FOREIGN PATENT DOCUMENTS

| | | |
|---|---|---|
| WO | 03/30787 A1 | 4/2003 |
| WO | 2012/118843 A1 | 9/2012 |
| WO | 2013/181375 A1 | 12/2013 |
| WO | 2015/057898 A1 | 4/2015 |
| WO | 2016/024248 A1 | 2/2016 |

OTHER PUBLICATIONS

Li et al., Tough adhesives for diverse wet surfaces, Science, 357(6349), 378-381, Jul. 2017.

* cited by examiner

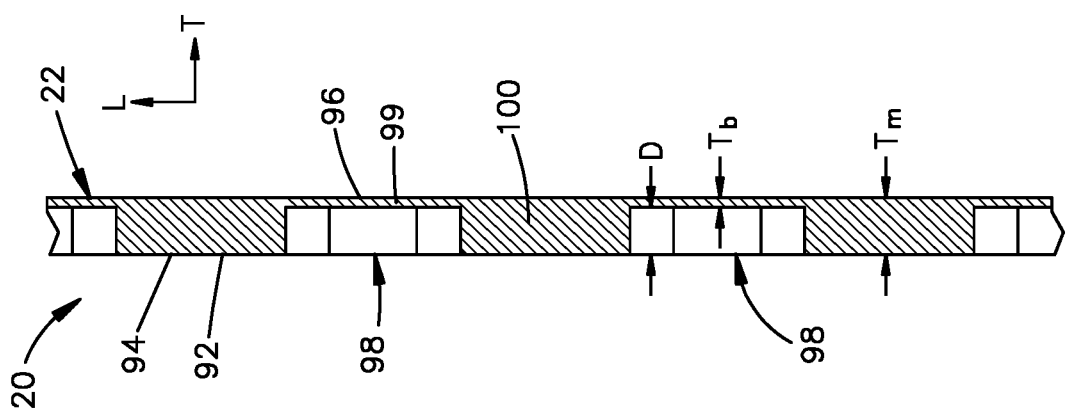
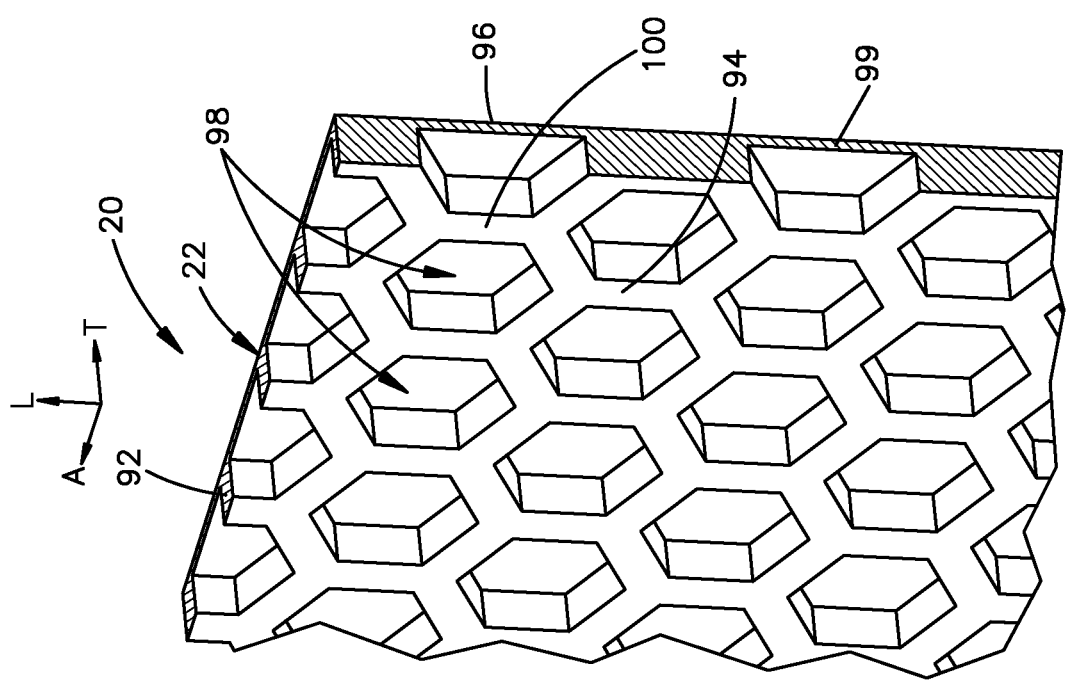
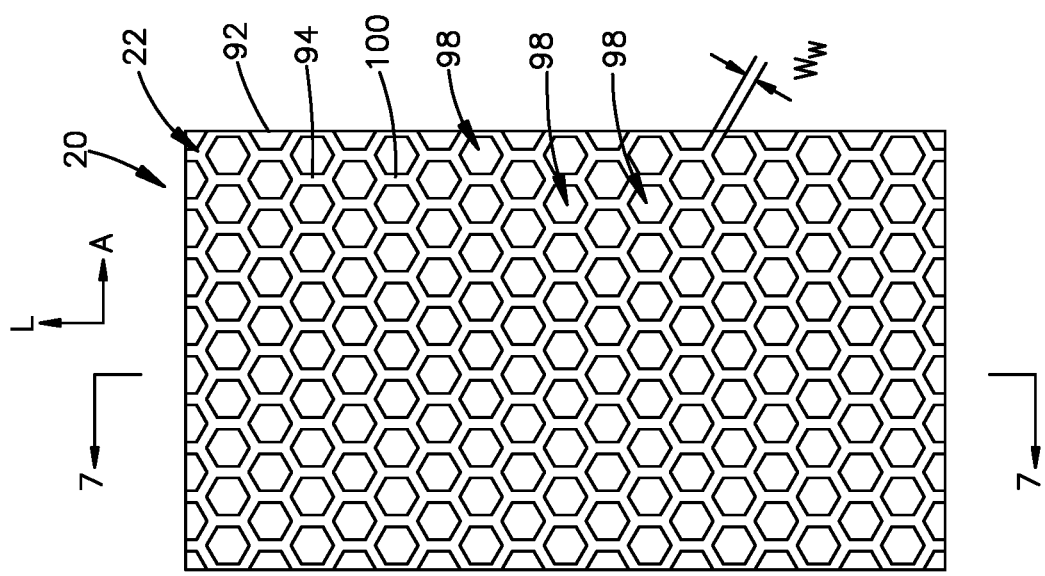

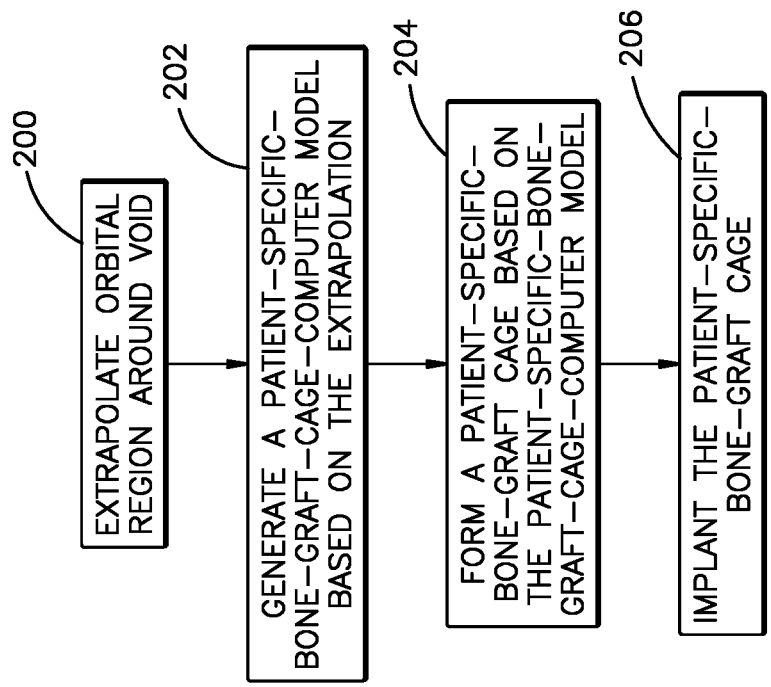
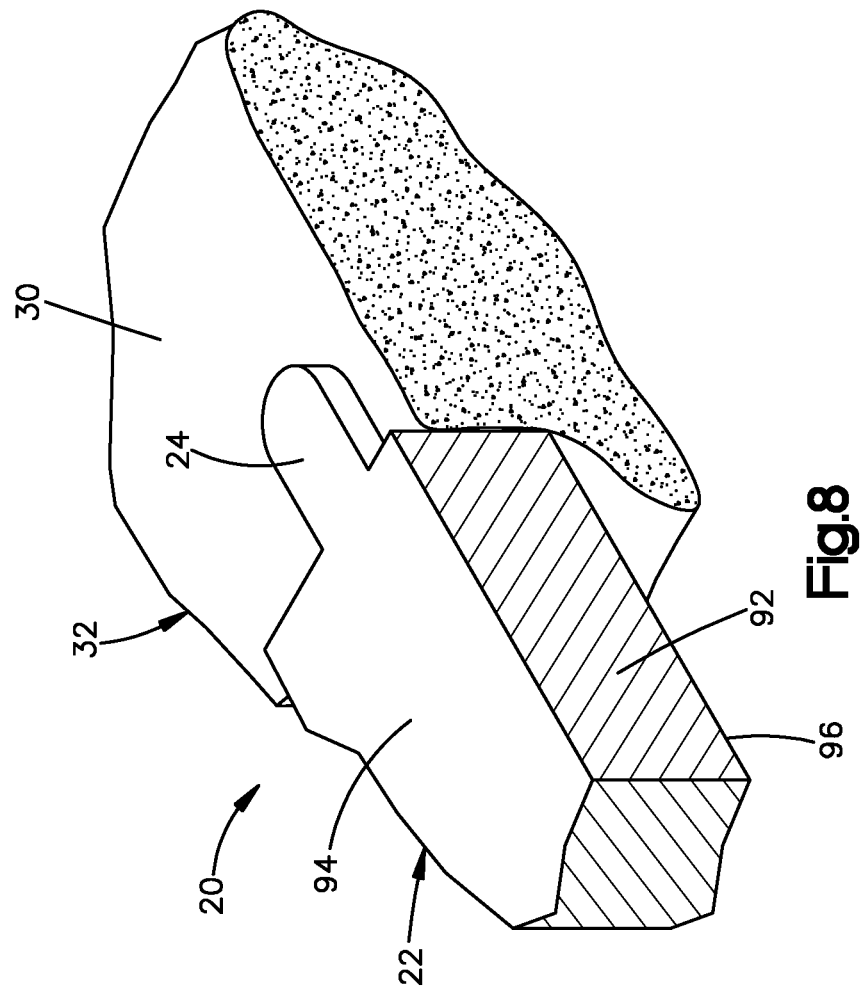

PATIENT SPECIFIC GRAFT CAGE FOR CRANIOMAXILLOFACIAL REPAIR

CROSS-REFERENCE TO RELATED APPLICATIONS

This Application claims the benefit of U.S. Provisional Application Ser. No. 63/057,913 filed Jul. 29, 2020, the contents of which is hereby incorporated by reference as if set forth in its entirety herein.

TECHNICAL FIELD

The present invention relates to a preformed implant (e.g., a patient-specific-bone-graft cage) for an orbital region which can be used as a replacement for a portion of, and optionally the entirety of, the orbital region.

BACKGROUND

Large bone defects can be treated with bone grafts to assist with healing. The bone grafts may be placed in the target area using any of a variety of methods. For example, a bone graft may simply be placed between two separated ends of an injured or otherwise damaged bone. However, without a container for the bone graft, the graft may fall away from a target site before it can be incorporated by the body into the healing bone.

For surgical treatment of fractures in the orbital region, bone grafts formed as meshes (e.g., with multiple through holes that together form a gridded pattern) made of titanium or other materials can be used. Intraoperatively, surgeons must fold and bend the meshes manually in order to reproduce the desired anatomical structures. Here, it is not always possible to reach, to clearly define, and to reconstruct anatomical structures that are deep inside of the orbital cavity (e.g., a bottom posterior portion of a patient's orbital cavity). Moreover, the result can significantly depend on the experience of the surgeon.

If a bone defect in a deeper part of the orbital cavity cannot be compensated for, the consequences can be double images (diplopia), sinking-in of the eye (enopthalmos) and disturbances of motility. In the worst case, excessive manipulation on the eye or on the optical nerve during the operation may result in the loss of sight.

By mirroring a three-dimensional ("3D") image of the patient's healthy (or undamaged) orbital bottom for use in creating a mesh for the other side (i.e., the unhealthy or damaged side) the meshes can be pre-formed as a replacement for a damaged orbital bottom. Similarly, a healthy medial orbital wall can be mirrored to create a pre-formed replacement of a damaged medial orbital wall on the other side. This mirroring technique can reduce modifications that the surgeon would otherwise be required to make if the mesh were, for example, flat or another shape significantly different from the portion of the orbital bottom or wall being replaced. However, the inventors of the present invention recognized that the surgeon may need to make modifications to such meshes to account at least for anatomical asymmetries between the patient's healthy orbital region and the existing orbital region (or surrounding bone) that is to receive the mesh.

SUMMARY

The present disclosure provides method of forming a patient-specific-bone-graft cage based on a patient-specific bone graft cage computer model that is based on a contour of a surface of the bone defining a void, and/or a patient-specific-bone-graft cage that includes a plurality of apertures, that terminate at a location between a front surface and a back surface of the patient-specific-bone-graft cage, for receipt of bone graft material. The patient-specific-bone-graft cage can construct an essential portion (including complex thin anatomical structures) of or substantially the entirety of the mid-face region (e.g., to fill a void in a damaged orbital region), which enables an improved structure reproduction and simplification for the surgeon. For example, the patient-specific-bone-graft cage may be formed based on the contour of the periphery defining the void in the damaged region, and require less modification by a surgeon compared to graft cages formed based only on mirroring techniques or normalized models.

The patient-specific-bone-graft cage may be formed as a single-piece of bioresorbable material. In some embodiments, the patient-specific-bone-graft cage is formed in multiple pieces that attach to one another. For example, the pieces may mechanically interconnect and/or may be adhered together. The pieces may form anatomical structures that define an opening for an optical nerve to pass through.

The apertures can provide space for receipt of bone graft material. The first surface of the patient-specific-bone-graft cage that defines a back of each aperture can provide support for bone graft material. Thus, bone graft material can be placed in the apertures and the risk of the bone graft material being undesirable displaced during or after implantation may be reduced, compared to mesh implants in which bone graft material is placed into through holes.

According to an embodiment of the present disclosure, a method of making a patient-specific-bone-graft cage computer model for forming a patient-specific-bone-graft cage to construct a portion of a mid-face region includes extrapolating a surface of a bone in the mid-face region wherein the surface defines a void in the mid-face region, and generating a patient-specific bone graft cage computer model based on the extrapolation of the surface of the bone. The patient-specific bone graft cage computer model is configured to match the extrapolation of the surface. The method may include forming a patient-specific-bone-graft cage based on the patient-specific bone graft cage computer model such that the patient-specific-bone-graft cage is configured to contact a periphery of the bone that defines the void when the patient-specific bone graft cage at least partially fills the void by constructing the portion of the mid-face region. For example, the patient-specific-bone-graft cage may be formed based on a subtraction of a 3D computer model, that represents the patient's existing bone structure, from a modified-computer model of the bone structure that includes the extrapolation. In an embodiment, the method does not require the extrapolating a surface step and/or the generating a patient-specific bone graft cage computer model step, or does not require the forming a patient-specific-bone-graft cage step.

According to another embodiment of the present disclosure, a patient-specific-bone-graft cage to at least partially fill a void in a mid-face region includes a membrane that includes a main body that defines a first surface and a second surface opposite the first surface and spaced from the first surface in a rearward direction. The main body includes a plurality of apertures that extends through the first surface along the rearward direction toward the second surface, and at least some of the apertures terminate at a base that is spaced from the second surface in a forward direction opposite the rearward direction, whereby the apertures provide space for receipt of bone graft material. In an embodiment, the membrane is flexible.

BRIEF DESCRIPTION OF THE DRAWINGS

The foregoing summary, as well as the following detailed description of illustrative embodiments of the patient-specific-bone-graft cage of the present application and the associated method, will be better understood when read in conjunction with the appended drawings. For the purposes of illustrating the patient-specific-bone-graft cage of the present application, there is shown in the drawings illustrative embodiments. It should be understood, however, that the application is not limited to the precise arrangements and instrumentalities shown. In the drawings:

FIG. 5 is a front view of a planarized section of the patient-specific-bone-graft cage of FIG. 3;

FIG. 6 is an oblique cross-sectional view of the section of the patient-specific-bone-graft cage of FIG. 5;

FIG. 7 is a cross-sectional side view of the section of the patient-specific-bone-graft cage of FIG. 5;

FIG. 8 is an enlarged cross-sectional oblique view of a portion of the patient-specific-bone-graft cage with a protrusion for mounting the patient-specific-bone-graft cage of FIG. 3; and FIG. 9 is a flow chart for a method of making the patient-specific-bone-graft cage of FIG. 1;

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The term "substantially," as used herein with respect to a parameter (e.g., shape, size, angle, dimension, direction, and the like) means the stated parameter as well as within +/−10%, such as +/−5%, for instance +/1 2%, including +/−1% of the stated parameter, unless otherwise indicated.

Figure 1:
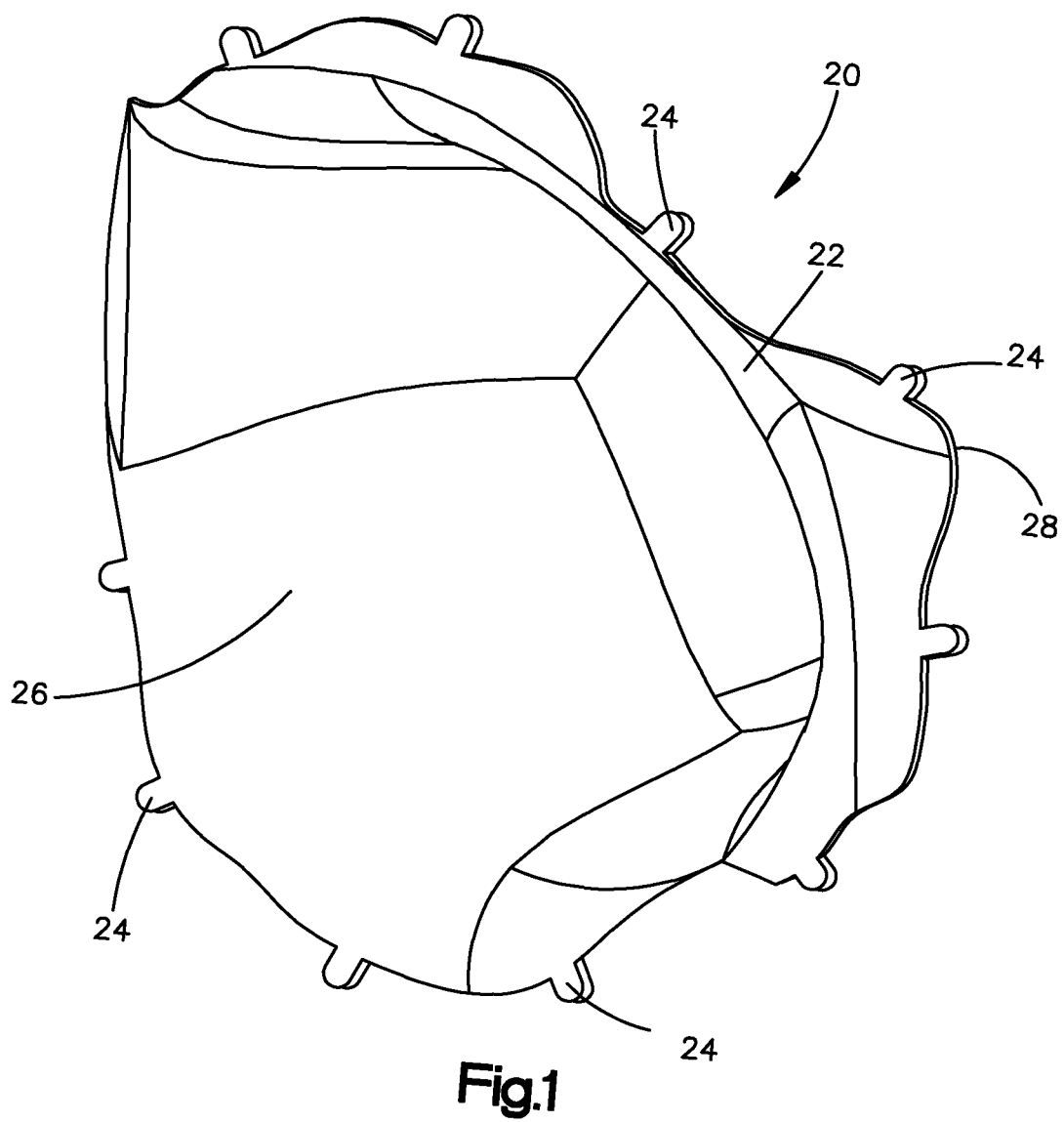
FIG. 1 is an oblique view of a patient-specific-bone-graft cage.

FIG. 1 illustrates an embodiment of a patient-specific-bone-graft cage 20. The patient-specific-bone-graft cage 20 may be bioresorbable. The patient-specific-bone-graft cage 20 may be formed as a single-piece of bioresorbable material. For example, a portion of or the entire patient-specific-bone-graft cage 20 may be made of Polycaprolactone. In an embodiment a portion of or the entire patient-specific-bone-graft cage is made of any of the biodegradable fiber reinforced composites disclosed in U.S. Publication No. 2004/0054372, filed Jul. 24, 2003 and entitled "Biodegradable Composites," which is incorporated herein by reference. As discussed below, in some embodiments, the patient-specific-bone-graft cage is formed by multiple pieces.

The patient-specific-bone-graft cage 20 may include a flexible membrane 22. The flexible membrane 22 may include multiple protrusions 24 that extend outwardly from an outer periphery of the flexible membrane 22 to provide surface area for mounting the patient-specific-bone-graft cage 20 (e.g., to a skull 30 (shown in FIG. 2)), as discussed further below. The flexible membrane 22 may be configured to construct (e.g., replace or reconstruct) anatomical structures of the skull 30 (shown in FIG. 2), and thereby fill a void 36 (shown in FIG. 2) when implanted. For example, the flexible membrane 22 may have a three-dimensional ("3D") shape that matches or substantially matches the 3D shape of the anatomical structures being replaced or reconstructed.

The flexible membrane 22 may define an inner surface 26 and an outer surface 28 that is opposite the inner surface 26. The inner surface 26 may generally define a shape or contour of one or more portions of anatomy that are damaged or missing, such as a concave portion of an orbit and/or adjacent anatomical structures (e.g., a portion of an orbital roof, an orbital bottom, a medial wall, and/or a lateral wall) as discussed further below. In an embodiment, the inner surface is defined by a single monolithic piece. In some embodiments, the inner surface is defined by multiple pieces that are joined together.

The outer surface 28 may extend along (e.g., parallel to) the inner surface 26 to define a shape or contour of one or more portions of anatomy that are damaged or missing, such as a convex portion of the orbit and/or adjacent anatomical structures (e.g., a portion of an orbital roof, an orbital bottom, a medial wall, and/or a lateral wall) as discussed further below. In an embodiment, the outer surface is defined by a single monolithic piece. For example, the outer surface and the inner surface may be defined by the same monolithic piece. In some embodiments, the outer surface is defined by multiple pieces that are joined together. In some embodiments, the outer surface defines a shape or contour that is different from the one or more portions of anatomy that are damaged or missing.

Figure 3:
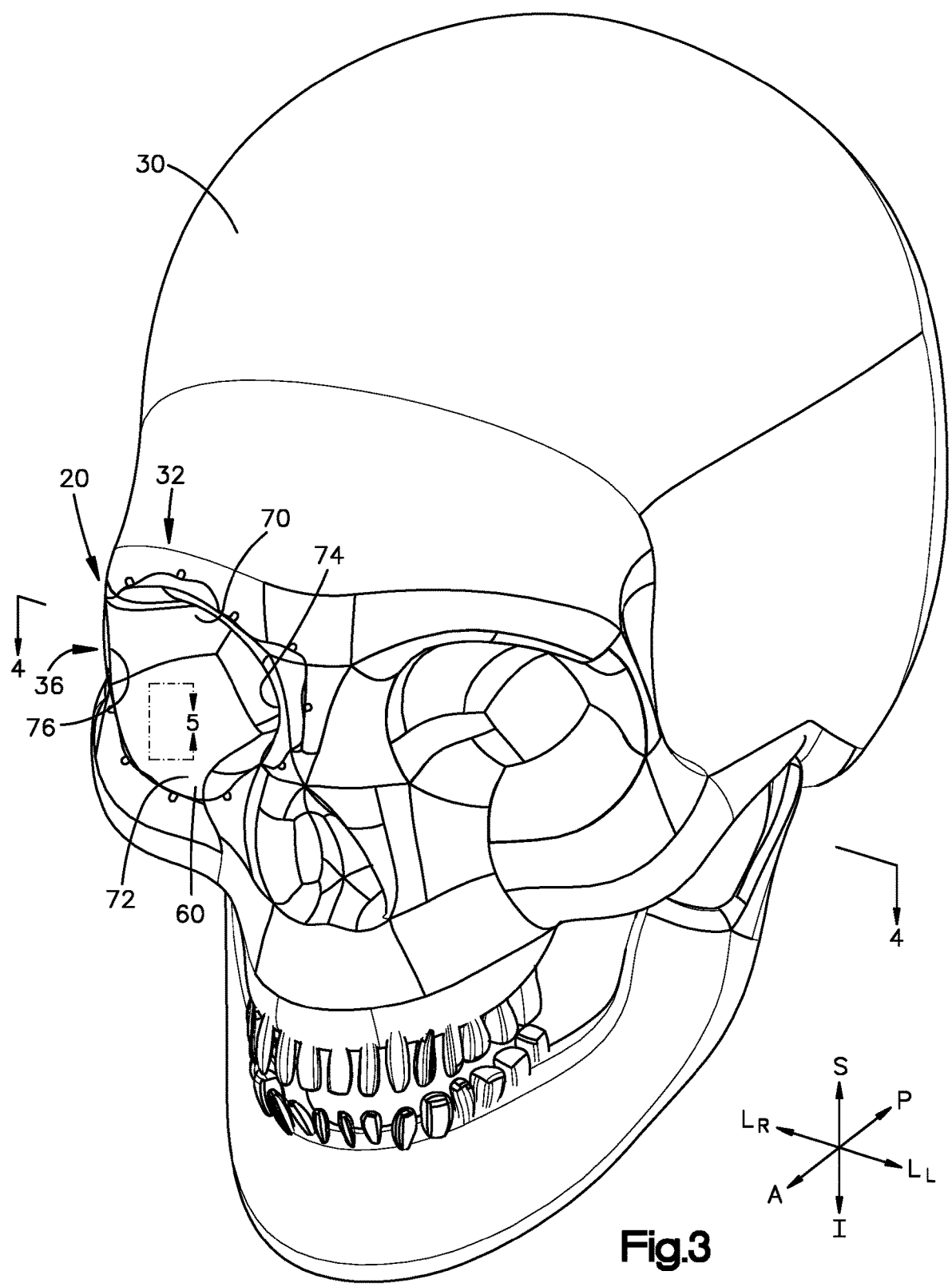
FIG. 3 is an oblique view of the skull of FIG. 2 in combination with the patient-specific-bone-graft cage of FIG. 1 that fills the void.

Certain terminology is used in the following description for convenience only and is not limiting. The words "right", "left", "lower," "upper," "back," and "front" designate directions in the drawings to which reference is made. The words "inner", "internal", and "interior" refer to directions towards the geometric center of the patient-specific-bone-graft cage 20, while the words "outer", "external", and "exterior" refer to directions away from the geometric center of the patient-specific-bone-graft cage 20. The words, "anterior", "posterior", "superior," "inferior," "medial," "lateral," and related words and/or phrases are used to designate various positions and orientations in the human body to which reference is made. When these words are used in relation to the patient-specific-bone-graft cage 20 or a component thereof, they are to be understood as referring to the relative positions of the patient-specific-bone-graft cage 20 as implanted in the body, for example, as shown in FIG. 3. The terminology includes the above-listed words, derivatives thereof and words of similar import.

Figure 2:
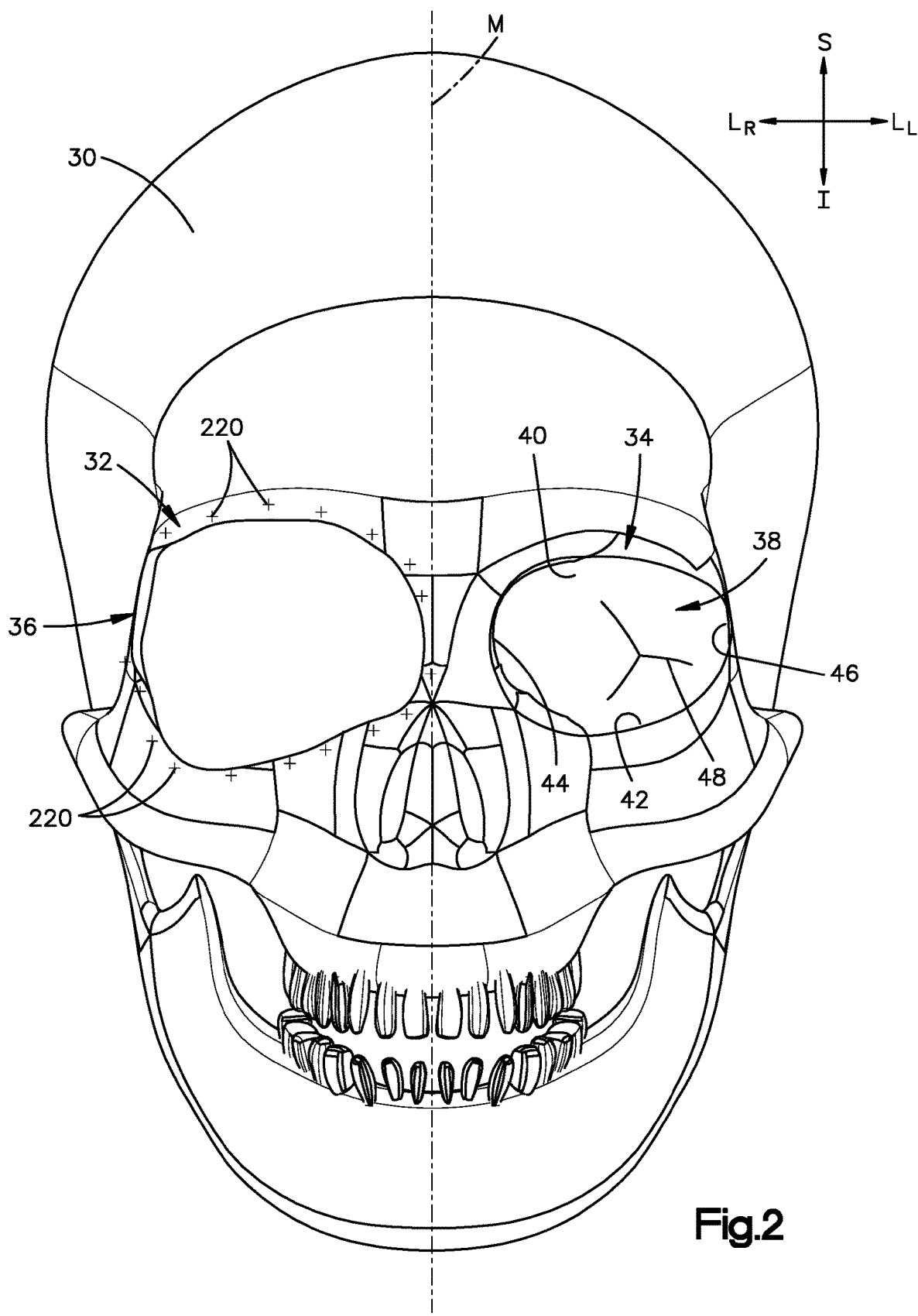
FIG. 2 is a front view of a skull with a void in a right orbital region of the skull.

Referring to FIG. 2, a skull 30 can extend along a lateral direction L, a vertical direction V, and an anterior-posterior direction A-P. The lateral direction L can include a right lateral direction $L_R$ and a left lateral direction $L_L$ that is opposite the right lateral direction. The vertical direction can include a superior direction S and an inferior direction I opposite the superior direction. The anterior-posterior direction can include a posterior direction P and an anterior direction A opposite the posterior direction (see FIG. 3). As shown in FIG. 2 a medial plane M that bisects the left and right sides of the skull 30 and extends orthogonally to the lateral directions $L_R$ and $L_L$. The medial plane M extends along both the vertical direction and the anterior-posterior direction.

As shown in FIG. 3, the lateral directions $L_R$ and $L_L$ are coaxial with one another along the lateral direction, the superior direction S and the inferior direction I are coaxial with one another along the vertical direction, and the posterior direction P and the anterior direction A are coaxial with one another along the anterior-posterior direction. Also, the lateral directions $L_R$ and $L_L$ are orthogonal to each of the superior direction S, the inferior direction I, the posterior direction P, and the anterior direction A. Moreover, the superior direction S and the inferior direction I are orthogonal with each of the posterior direction P and the anterior direction A.

Referring again to FIG. 2, the skull 30 has a right orbital region 32 (on the left side of the page illustrating FIG. 1) and a left orbital region 34 (on the right side of the page illustrating FIG. 1). The left orbital region 34 is healthy and whole, whereas the right orbital region 32 has a bone defect. In one example, the bone defect is configured as the void 36 instead of one or more anatomical structures that correspond to each of those of the left orbital region 34. Alternatively or additionally, the bone defect can include one or more fractures in one or more orbital anatomical structures.

In one example, the left orbital region 34, being a normalized healthy human orbital region, is defined by a portion of multiple anatomical structures including a frontal bone, a maxilla, a zygomatic bone, a lacrimal bone, a nasal bone, a sphenoid bone, an ethmoid bone, and a palatine bone. Since the skull 30 is a simplified representation of an actual human skull, some of the above anatomical structures are not expressly identified (and in some cases are omitted or simplified to facilitate understanding of the technological advancements of the present disclosure).

An orbit 38 of the left orbital region 34 includes an orbital roof 40 (also referred to as a "superior wall"), an orbital bottom 42 (also referred to as an "inferior wall"), a medial wall 44, and a lateral wall 46. The orbital roof 40 is formed primarily by an orbital plate of the frontal bone and a lesser wing of the sphenoid bone near an apex of the orbit 38.

The orbital bottom 42 is formed by an orbital surface of the maxilla, an orbital surface of the zygomatic bone, and a minute orbital process of the palatine bone. The orbital bottom 40 is separated from the lateral wall 46 by an inferior orbital fissure 48. The orbital bottom 42 elevates with a convex curvature such that a posterior medial part of the orbital bottom 42 is higher than an anterior lateral part of the orbital bottom 42.

The medial wall 44 is formed primarily by the orbital plate of the ethmoid bone, as well as portions of a frontal process of the maxilla, the lacrimal bone, and a small part of the sphenoid bone. A central part of the medial wall 44 is thin and steeply declines to the orbital bottom 42.

The lateral wall 46 is formed by a frontal process of the zygomatic bone and posteriorly formed by an orbital plate of a greater wing of the sphenoid bone. The lateral wall 46 is the thickest wall of the orbit 38. Any one or more of these structures can be damaged or missing so as to create a void that is designed to be substantially filled by the cage 20.

Turning again to FIGS. 3 and 4, the patient-specific-bone-graft cage 20 is configured to be inserted into the void 36 of the skull 30. The patient-specific-bone-graft cage 20 may be mounted to peripheral portions of the skull 30. As discussed further below with regard to manufacturing the patient-specific-bone-graft cage 20, the patient-specific-bone-graft cage 20 may form a reconstruction of each missing portion of the right orbital region 32.

The patient-specific-bone-graft cage 20 may form at least a portion of a replacement for each missing part of the anatomical structure for reconstruction. For example, the patient-specific-bone-graft cage 20 forms at least a portion of a reconstructed orbit 60 for reconstruction of the right orbital region 32. The reconstructed orbit 60 may include a reconstructed orbital roof 70, a reconstructed orbital bottom 72, a reconstructed medial wall 74, and a reconstructed lateral wall 76. The inner surface 26 may form an anterior facing portion of the reconstructed orbit 60. In an embodiment, the reconstructed orbit includes a portion or entirely of any one of or any combination of the reconstructed orbital roof 70, the reconstructed orbital bottom 72, the reconstructed medial wall 74, and the reconstructed lateral wall 76.

Figure 4:
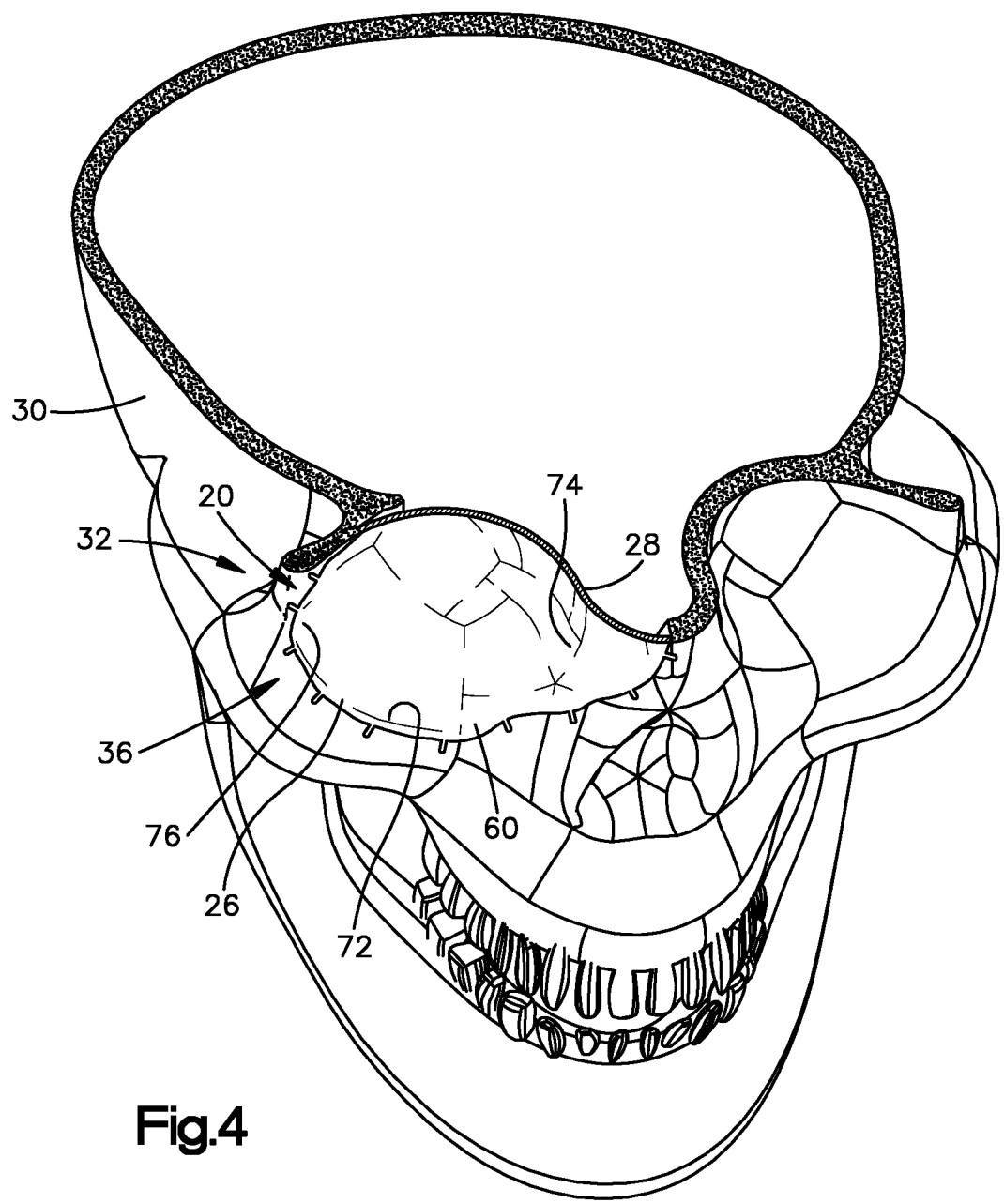
FIG. 4 is an oblique cross-sectional view of the combination of the patient-specific-bone-graft cage and skull of FIG. 3.

Turning to FIGS. 5-7, a planarized representation of a portion of the flexible membrane 22 of the patient-specific-bone-graft cage 20 is illustrated, it being appreciated that either upon being manufactured or during use the flexible membrane 22 may be contoured to fit into the void 36 and form a shape for reconstructing at least a portion of the orbital region 32 (shown in FIG. 4). The portion of the flexible membrane 22 has a length that is elongate along a longitudinal direction L, has a width along a lateral direction A that is perpendicular to the longitudinal direction L, and has a thickness along a transverse direction T that is perpendicular to both the longitudinal direction L and the lateral direction A. The length can be greater than the width, and the width can be greater than the thickness. In an embodiment, when the patient-specific-bone-graft cage 20 is implanted into an orbital region, the transverse direction T is parallel with the anterior-posterior direction A-P (shown in FIG. 3), the longitudinal direction L is parallel with the vertical direction V (shown in FIG. 3), and/or the lateral direction A is parallel with the lateral direction L (shown in FIG. 3).

In actual use, the portion of the flexible membrane 22 illustrated in FIGS. 5-7 may be manufactured with (or manipulated by a surgeon after manufacturing to have) the appropriate complex curved shape that a corresponding portion of the orbital region would be expected to have, if that portion of the orbital region were not missing (e.g., prior to the orbital region being damaged). For example, the flexible membrane 22 may define a 3D contour that matches a 3D contour of an extrapolation, of existing bone around the void 36 (shown in FIG. 2), that extends through the void 36.

The flexible membrane 22 may include a main body 92 that defines a front surface 94 (an example of a "first surface") and a back surface 96 (an example of a "second surface") that is opposite the front surface 94 along the transverse T direction. The front surface may face a forward direction along the transverse direction T, and the back surface may face a rearward direction that is opposite the forward direction along the transverse direction T.

The front surface 94 may define the inner surface 26 (see FIG. 4) and the back surface 96 may define the outer surface 28 (see FIG. 4). For example, the front surface 94 and the back surface 96 may together define the entire reconstructed orbit 60, including the reconstructed orbital roof 70, the reconstructed orbital bottom 72, the reconstructed medial wall 74, and the reconstructed lateral wall 76 as a single monolithic piece. In an embodiment, the front surface 94 forms a portion of the reconstructed orbit, for example, a portion of or the entirely of the reconstructed orbital roof, the reconstructed orbital bottom, the reconstructed medial wall, and/or the reconstructed lateral wall. In some embodiments, the front surface and/or the back surface are formed by multiple distinct pieces. For example, each portion of the reconstructed orbit (e.g., a portion of or the entirely of the reconstructed orbital roof, the reconstructed orbital bottom, the reconstructed medial wall, and/or the reconstructed lateral wall) may be formed by a distinct piece.

The flexible membrane 22 may be flexible from an unflexed position to a flexed position. Flexing of the flexible membrane 22 may facilitate contouring and/or implantation of the flexible membrane 22.

For example, the front surface 94 and the back surface 96 are illustrated as being planar and parallel with a plane defined by the longitudinal direction L and the lateral direction A in the flat position. When in the flat position, the flexible membrane 22 may be transitioned to the flexed position such that the front surface 94 and the back surface 96 are non-planar to conform to the contour of the replaced or reconstructed anatomical structure. In an embodiment, the front surface and the back surface are contoured to match or substantially match the contour of the of the replaced or reconstructed anatomical structure when in the unflexed position, and the flexible membrane may be transitioned to the flexed position.

The flexible membrane 22 may include a plurality of apertures 98 that are defined by the main body 92. The apertures 98 provide space to receive bone graft material. For example, the apertures 98 may extend from the front surface 94 to the back surface 96. Some or all of the apertures 98 may terminate at a location spaced from the back surface 96 in the forward direction. The apertures 98 may have a recessed depth D of 1.2 millimeter (mm) to 4.2 mm. In an embodiment, at least some or all of the apertures are open at the front and the back, that is the apertures are through holes that extend along the transverse direction T through the front surface and the back surface of the main body. In some embodiments, the front surface and/or the back surface partially close or entirely close one or more of the apertures.

The main body 92 defines a base 99 of the apertures 98 that is disposed between the front surface 94 and the back surface 96. For example, the apertures 98 may be open from the front surface 94 to the base 99 in the rearward direction.

The apertures 98 may have a hexagonal shape in a cross-sectional plane that is perpendicular to the transverse direction T. The shape may be substantially uniform along the depth D. In another embodiment, some or all of the apertures have a different cross-sectional shape. In some embodiments, the cross-sectional shape of some or all of the apertures varies along the depth of the apertures.

The apertures 98 may be separated from one another by at least one side wall 100 of the main body 92. The side wall 100 may extend from the front surface 94 to the base 99. The side wall can be curved, for instance, to define an oval, circular, or other curved shape of the aperture in the cross-sectional plane. Or the flexible membrane 22 may include a plurality of side walls 100 that combine to define a shape, such as a hexagon, a square, an octagon, a triangle, a rectangle, or any other regular or irregular geometric shape as desired, in the cross-sectional plane.

The side wall 100 may uniformly separate each of the apertures 98 from one another. For example, each aperture 98 may be spaced from each adjacent aperture 98 by a wall width $W_w$ of 0.8 mm. In another embodiment, the wall width $W_w$ is substantially 0.8 mm.

The flexible membrane 22 includes a plurality of interconnected side walls 100. Each of the side walls 100 has a first side and a second side opposite the first side. The first side may define at least a portion of one of the apertures 98. The second side may define at least a portion of another one of the apertures 98.

Each of the side walls 100 may be straight and angled with respect to any adjacent connected side walls 100. For example, multiple adjacent side walls 100 combine to define the outer perimeters of a corresponding aperture 98. These side walls 100 form a hexagonal shape perpendicular to the transverse direction T.

In another embodiment, the apertures may be arranged relative to one another in a different pattern than that shown in FIGS. 5-7. In some embodiments, adjacent apertures are separated by multiple different walls.

Referring now to FIGS. 6 and 7, the flexible membrane 22 may have a total thickness $T_m$ of 2.0 mm to 5.0 mm. In another embodiment, the flexible membrane has a total thickness $T_m$ of about 2.0 mm to about 5.0 mm.

The main body 92 may have a thickness at the wall 100 that is equal to the total thickness $T_m$. At the apertures 98, on the other hand, the thickness $T_b$ of the main body 92 may be significantly reduced. For example, the main body 92 has a thickness $T_b$ of 0.8 mm behind at least one of the apertures 98 of the plurality of apertures. The recessed depth D may be dependent upon the total thickness $T_m$ and the thickness $T_b$. For example, the recessed depth D may be 0.8 mm less than the total thickness $T_m$ in various embodiments. In an embodiment, the thickness $T_b$ is about 0.8 mm.

Turning now to FIG. 8, an enlarged cross-sectional oblique view of a portion of the patient-specific-bone-graft cage 20 and the skull 30 is illustrated. One of the protrusions 24 extends beyond a portion of an end, of the main body 92, that extends between the front surface 94 and the back surface 96. The protrusion 24 is mounted to the existing bone of the orbital region 32 of the skull 30. More than one or all of the protrusions 24 may extend beyond the corresponding portion of the end of the main body 92 in the same or similar manner as the protrusion 24 illustrated in FIG. 8.

For example, the protrusions 24 may each extend from a corresponding portion of the end of the main body 92. The protrusions 24 may each be elongated in a direction parallel to the respective adjacent portion of the front surface 94 and away from the respective portion of the end of the main body 92. In an embodiment, some or all of the protrusions are each elongated in a direction that is non-parallel to the adjacent portion of the front surface and/or the back surface. In some embodiments, some or all of the protrusions each extend from the front surface.

Some or all of the protrusions 24 may extend from a corresponding side wall 100 to mount to the existing bone of the orbital region 32 of the skull 30. For example, the outermost apertures 98 that are adjacent to the end of the main body 92 may be at least partially defined by respective outermost side walls 100. The protrusions 24 may extend from a portion of a corresponding outermost side wall 100.

Bio resorbable adhesive may be disposed on a back side of each protrusion 24, between each protrusion 24 and the existing bone of the orbital region 32, for adhering the at least one protrusion to the outer surface of the orbital region. The back side of each protrusion 24 may face in the same or substantially the same direction as the back surface 96. In an embodiment, the bio resorbable adhesive includes two layers: 1) an adhesive surface including an interpenetrating positively charged polymer, and 2) a dissipative matrix. See e.g., Li, J., Celiz et al. (2017). Tough adhesives for diverse wet surfaces. Science (New York, N.Y.), 357(6349), 378-381. https://doi.org/10.1126/science.aah6362, which is incorporated herein by reference; see also, H. Cho et al. Intrinsically reversible superglues via shape adaptation inspired by snail epiphragm, *Proceedings of the National Academy of Sciences of the United States of America*. Vol. 116, Jul. 9, 2019, p. 13774. doi: 10.1073/pnas.1818534116.

In some embodiments, the bio resorbable adhesive is disposed between the flexible membrane and other portions of the existing bone to adhere the flexible membrane directly to the existing bone of the orbital region.

The depth, contour, and thickness of the structures of the right orbital region 32 are parameters that may individually vary depending on the person. The parameters may be determined by an examination before the patient-specific-bone-graft cage 20 is formed. For example, a 3D imaging system (e.g., a computed tomography ("CT") scanner) can scan a given patient's skull (e.g., the skull 30 shown in FIG. 2) to generate a 3D computer model—a virtual model—of the entire skull 30 or a portion of the skull 30.

In some embodiments, an initial-mirrored-computer model of the patient's bone structure may be generated by mirroring a 3D image of the unaffected (e.g., healthy and undamaged) side to the affected (e.g., damaged) side. For example, a computer with 3D shape analysis and morphometrics software (e.g., Scalismo—Scalable Image Analysis and Shape Modelling, or Geomagic® Freeform) could, in the case of the skull 30 in FIG. 2, load the 3D image of the skull 30. The 3D shape analysis and morphometrics software can mirror the image of the left side—the healthy side—of the skull 30 to the right side of the 3D image of the skull 30 to generate the initial-mirrored-computer model.

This mirroring technique thus can result in an initial-computer model that has a symmetrical right and left side. Accordingly, the orbital region of the initial-computer model's right side does not include a representation of the void 36 shown in FIG. 2. However, the patient's skull 30 may not be entirely symmetrical. Thus, a bone-graft cage formed based entirely on the initial-mirrored-computer model and the periphery of the bone defining the void 36 may require modification by a surgeon to match the contour of the bone defining the void 36 or to account for other asymmetries of structures of or in the patient's skull 30. As noted below, in some embodiments, the initial-computer model is a statistical shape model, a Gaussian process model, or a principal component model generated by 3D shape analysis and morphometrics software, and is not based on an initial-mirrored-computer model.

Turning now to FIG. 9 with reference to FIG. 2, a method of making and using the patient-specific-bone-graft cage 20 is represented as a series of steps 200-206. An extrapolation of the bone defining the void 36 (shown in FIG. 2) may be generated in step 200 based on the contours of the periphery of the right orbital region 32 that defines the void 36. For example, multiple landmark locations 220 (exemplified in FIG. 2) can be identified on the periphery of the right orbital region 32 that defines the void 36. The landmark locations 220 may be chosen automatically by the 3D shape analysis and morphometrics software and/or manually by a user to map the contours of the surface of the right orbital region 32 defining the void 36.

The 3D shape analysis and morphometrics software may generate a principal component model based on a principal component analysis of the landmark locations 220. In an embodiment, the 3D shape analysis and morphometrics software generates a statistical shape model or a Gaussian process model based on the landmark locations.

At step 202, a patient-specific bone graft cage computer model may be generated based on the extrapolation. For example, the 3D shape analysis and morphometrics software may modify the initial-mirrored-computer model based on the extrapolation to generate a modified-computer model of the skull 30 including a virtual modification to the right orbital region 32. The 3D shape analysis and morphometrics software may generate an initial-patient-specific bone graft cage computer model that is based on the modified-computer model of the skull 30 and the void 36. For example, the 3D computer model that represents the patient's existing bone structure (e.g., of the mid-face region or the entire skull 30) may be subtracted from the modified-computer model of the skull 30 to generate the initial-patient-specific bone graft cage computer model.

Accordingly, the initial-patient-specific bone graft cage computer model may be tailored to the right orbital region 32 and thus account for asymmetries between the right orbital region 32 and the left orbital region 34. For example, the initial-patient-specific bone graft cage computer model may include an orbit that includes an orbital roof, an orbital bottom, a medial wall, and a lateral wall that significantly correspond in shape and size to the orbital roof 40, the orbital bottom 42, the medial wall 44, and the lateral wall 46 identified in FIG. 2—but with some variations that account for asymmetries in the shape and size of the right orbital region 32.

In another embodiment, the initial-normalized-computer model may be generated based on a normalized model of the bone structure (e.g., a normalized skull). Similar to the initial-mirrored-computer model discussed above, the initial-normalized-computer model may be generated and modified based on the extrapolation to generate an initial-patient-specific bone graft cage computer model. In some embodiments, the extrapolation itself serves as the entire basis for generating the initial-patient-specific bone graft cage computer model. For example, as noted above, the initial-patient-specific bone graft cage computer model may not be based on an initial-mirrored-computer model and/or may not be based on an initial-normalized-computer model.

Referring briefly to FIGS. 5-7, the initial-patient-specific bone graft cage computer model may be weakened by incorporating apertures corresponding to the apertures 98. As a result, a weakened-patient-specific bone graft cage computer model may be generated.

Referring briefly to FIGS. 1 and 8, the user can incorporate patient-specific mounting structures into the weakened-patient-specific-bone-graft-cage-computer model to result in the patient-specific bone graft cage computer model. For example, the user may add protrusions—to the weakened-patient-specific bone graft cage computer model—corresponding to the protrusions 24, based on the contour of the corresponding right orbital region 32. In an embodiment, mounting structures are not incorporated into the weakened-patient-specific bone graft cage computer model. In some embodiments, the patient-specific mounting structures are incorporated into the initial-patient-specific bone graft cage computer model. In some embodiments, the patient-specific mounting structures are incorporated into the initial-patient-specific bone graft cage computer model before weakening of the resulting computer model, or the resulting computer model is not weakened.

In some embodiments, the patient-specific bone graft cage computer model includes further user modifications. For example, the patient-specific bone graft cage computer model may include a preset breaking line at a transition of the medial wall and the orbital bottom that is manually added by the user. This breaking line may run in the direction of the optic nerve. In some embodiments, the 3D shape analysis and morphometrics software automatically generates the entirety of the reconstructed anatomical structures, including at least one canal for a nerve.

In an embodiment, the patient-specific bone graft cage computer model does not include apertures. In another embodiment, the patient-specific bone graft cage computer model does not include the mounting portions. In yet another embodiment, the patient-specific bone graft cage computer model is the initial-patient-specific bone graft cage computer model.

Referring again to FIG. 9, at step 204, the patient-specific-bone-graft cage 20 may be formed based on the patient-specific bone graft cage computer model. For example, the entire patient-specific bone graft cage computer model may be 3D printed with a bio resorbable material to form the patient-specific-bone-graft cage 20 as a single monolithic piece. In some embodiments, the patient-specific-bone-graft cage is printed in multiple pieces that attach to one another. For example, the pieces may be formed with mechanical attachment structures that enable the pieces to be attached to one another, and/or the pieces may be adhered together.

Referring now to FIGS. 3, 6, and 9, at step 206, the patient-specific-bone-graft cage 20 is implanted into the right orbital region 32 to at least partially or entirely fill the void 36. For example, the bone graft material may be inserted into each of the apertures 98 prior to insertion of the patient-specific-bone-graft cage 20 into the right orbital region 32. The bone graft material may substantially fill each of the apertures 98.

The patient-specific-bone-graft cage 20 with the bone graft material may be placed into the void 36. For example, the back surface 96 and/or the protrusions 24 are placed into contact with a periphery of the human skull 30 that defines the void 36, as shown in FIG. 3. In an embodiment, the patient-specific-bone-graft cage is placed into the void without bone graft material. For example, the bone graft material may be inserted into each of the apertures while the patient-specific-bone-graft cage is inside the void.

In some embodiments, an anti-infectant (e.g., an antibiotic) is combined with the patient-specific-bone-graft cage 20. For example, the anti-infectant may be placed in the apertures 98. In an embodiment, the anti-infectant is mixed with the bone graft material, which may be stem cell based, allograft based, and/or synthetic. Alternatively or additionally, the anti-infectant may coat an entirety of, or at least a portion of, the patient-specific-bone-graft cage 20.

The bio resorbable adhesive may be applied to surfaces of the protrusions 24 and/or the flexible membrane 22 that contact a surface of the right orbital bone region 32 to secure the patient-specific-bone-graft cage 20 to the right orbital bone region 32 in the position shown in FIG. 3. The bio resorbable adhesive may prevent the patient-specific-bone-graft cage 20 from moving relative to the right orbital bone region 32.

Figure 10:
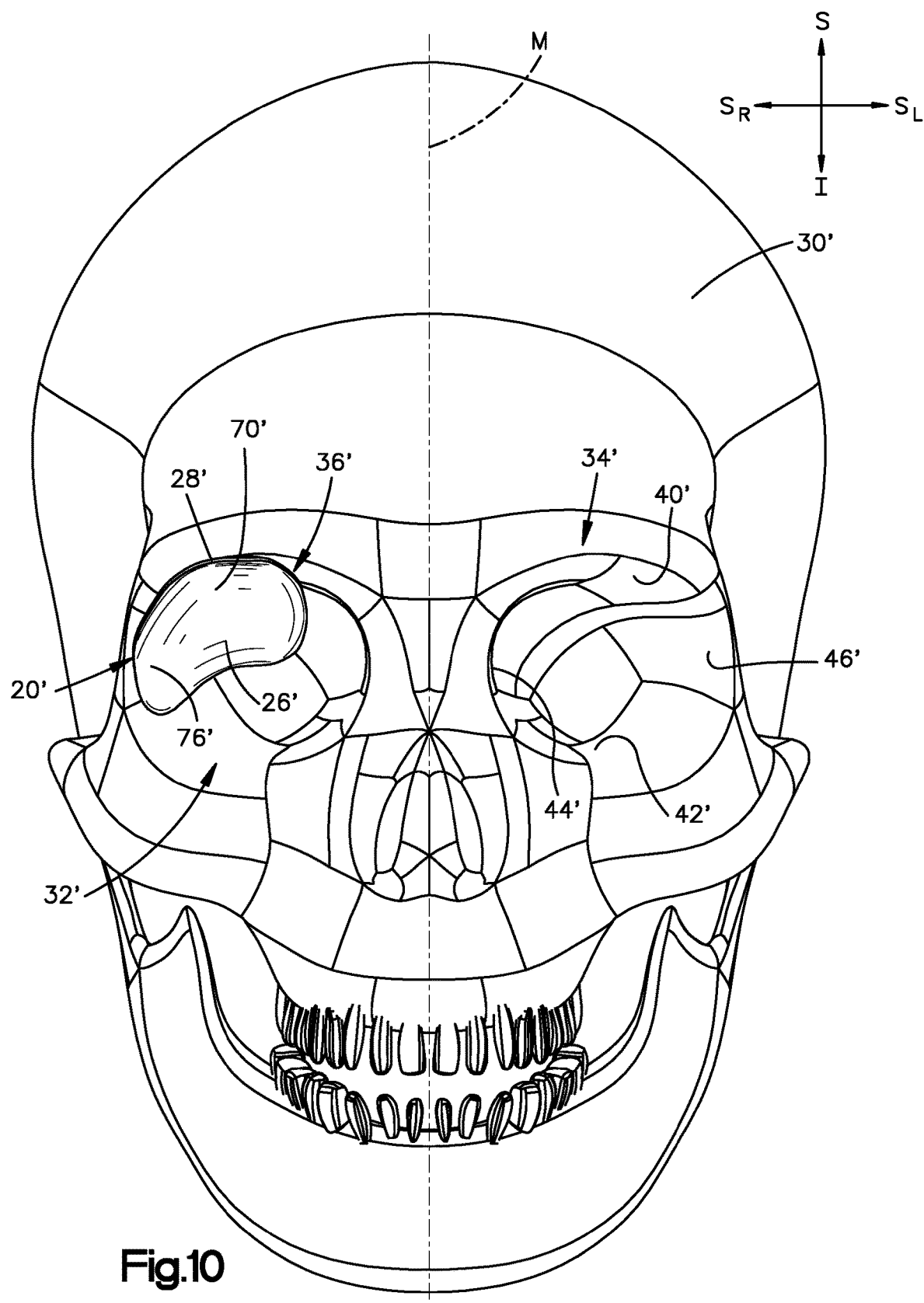
FIG. 10 is a front view of a skull in combination with another embodiment of the patient-specific-bone-graft cage that fills a void in the skull.

Referring now to FIG. 10, a second embodiment of the patient-specific-bone-graft cage is identified as 20' and may be implanted in a skull 30'. It is to be appreciated that the patient-specific-bone-graft cage 20' can be similar to the first embodiment of the patient-specific-bone-graft cage 20 shown in FIG. 1, and the skull 30' can be similar to the skull 30 shown in FIG. 2. Accordingly, the same reference numbers used above with reference to the first embodiment can be also used with a prime notation in reference to second embodiment. It is also to be appreciated that, unless otherwise set forth below, the components (and features thereof) of the patient-specific-bone-graft cage 20' and skull 30' can be similar to or the same as those of the patient-specific-bone-graft cage 20 and skull 30.

The skull 30' includes a left orbital region 34' that is healthy and whole, whereas the right orbital region 32' has a bone defect configured as a void 36' instead of one or more anatomical structures that correspond to each of those of the left orbital region 34'. For example, the left orbital region 34' includes an orbital roof 40' (also referred to as a "superior wall"), an orbital bottom 42' (also referred to as an "inferior wall"), a medial wall 44', and a lateral wall 46'. The void 36' of right orbital region 32', on the other hand, may be present instead of at least a portion of a corresponding orbital roof and lateral wall.

The patient-specific-bone-graft cage 20' may be inserted in the void 36'. For example, the patient-specific-bone-graft cage 20' may be mounted to peripheral portions of the skull 30. Adhesive may adhere the patient-specific-bone-graft cage 20' to the peripheral portions of the skull 30', without a separate fastener attaching the patient-specific-bone-graft cage 20' to the skull 30'.

The patient-specific-bone-graft cage 20' may form a reconstruction of each missing portion of the right orbital region 32'. For example, the patient-specific-bone-graft cage 20' may form at least a portion of a reconstructed orbital roof 70' and lateral wall 76'. An inner surface 26' and an outer surface 28' (shown best in FIG. 11) of the patient-specific-bone-graft cage 20' may together form at least portion of or substantially an entirety of the reconstructed orbital roof 70' and the reconstructed lateral wall 76'. In an embodiment, the patient-specific-bone-graft cage forms a portion or entirely of any one of or any combination of the reconstructed orbital roof, a reconstructed orbital bottom, a reconstructed medial wall, and/or the reconstructed lateral wall.

The patient-specific-bone-graft cage 20' may be formed using the same or similar methods discussed above with reference to the patient-specific-bone-graft cage 20 and FIG. 9. For example, a statistical shape model, a Gaussian process model, or a principal component model may be generated by 3D shape analysis and morphometrics software based on the contour of the periphery of the skull 30' defining the void 36'. The generated model may not based on a mirroring technique and/or may not be based on a normalized skull.

The patient-specific-bone-graft cage 20' may be bioresorbable. For example, the entire patient-specific-bone-graft cage 20' may be formed as a single-piece of bioresorbable material, such as Polycaprolactone.

Figure 11:
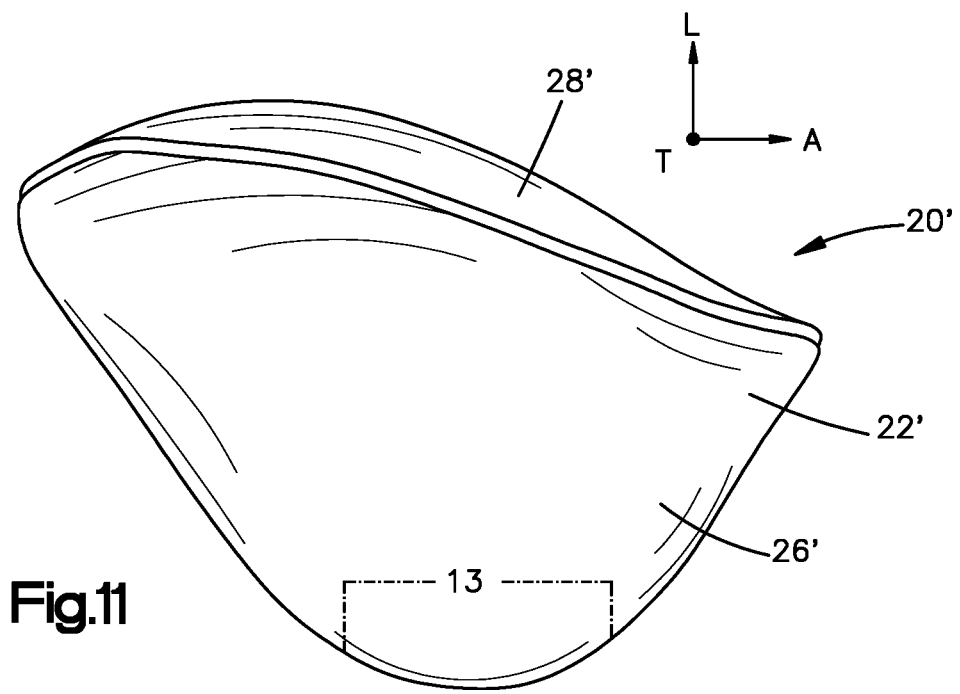
FIG. 11 is a front oblique view of the patient-specific-bone-graft cage of FIG. 10.
Figure 12:
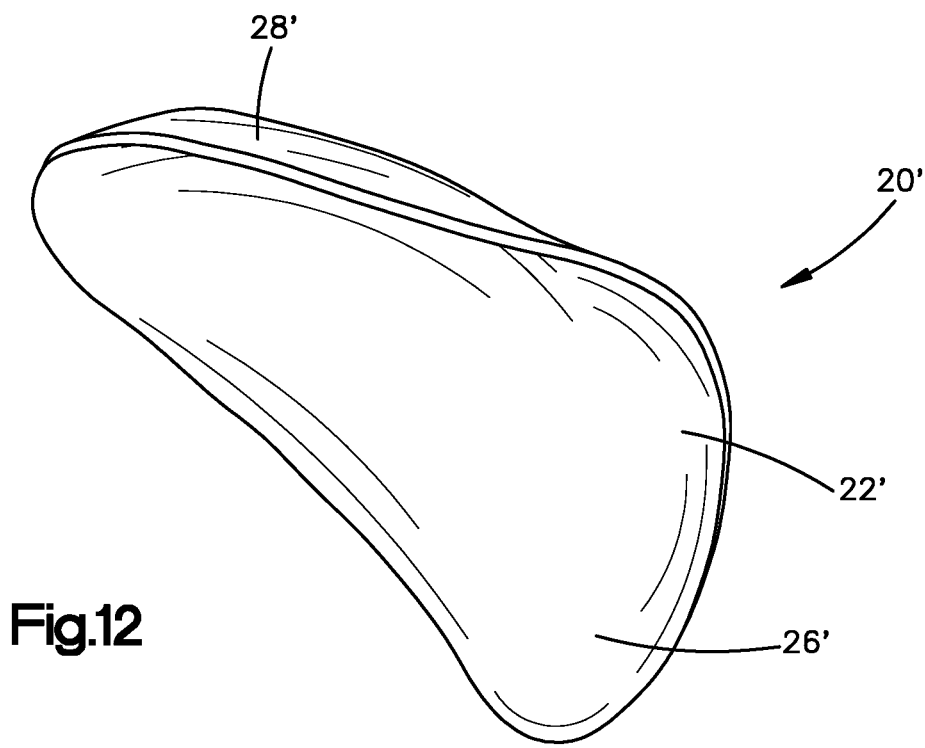
FIG. 12 is a side oblique view of the patient-specific-bone-graft cage of FIG. 10.

Turning to FIGS. 11 and 12, the patient-specific-bone-graft cage 20' may include a flexible membrane 22' that has a three-dimensional ("3D") shape that matches or substantially matches the 3D shape of the anatomical structures being replaced or reconstructed. In some embodiments, the flexible membrane includes protrusions extend outwardly from an outer periphery of the flexible membrane to provide surface area for mounting the patient-specific-bone-graft cage.

The flexible membrane 22 may define the inner surface 26' and the outer surface 28' that is opposite the inner surface 26'. For example, the inner surface 26' may define a concave portion and the outer surface 28' may define a convex portion opposite the concave portion.

The flexible membrane 22' may have a length that is elongate along a longitudinal direction L, has a width along a lateral direction A that is perpendicular to the longitudinal direction L, and has a thickness along a transverse direction T that is perpendicular to both the longitudinal direction L and the lateral direction A. For example, the flexible membrane 22' may define a 3D contour that matches a 3D contour of an extrapolation, of existing bone around the void 36' (see FIG. 10), that extends through the void 36'.

The length and width can be greater than the thickness. In an embodiment, when the patient-specific-bone-graft cage 20' is implanted into an orbital region, the transverse direction T is parallel with the lateral direction L, the longitudinal direction L is parallel with the vertical direction V, and/or the lateral direction A is parallel with the anterior-posterior direction A-P.

Figure 13:
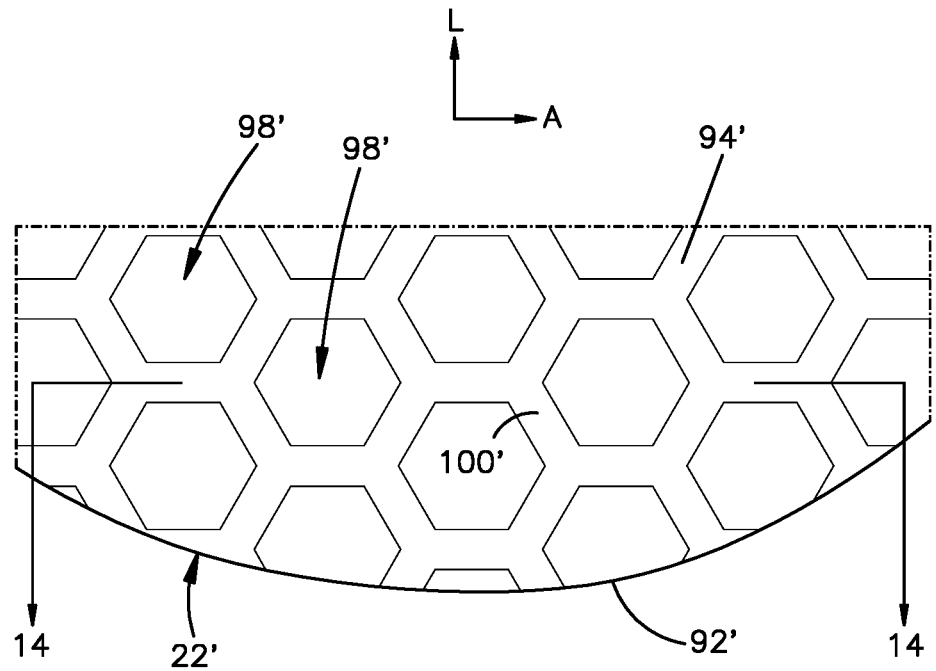
FIG. 13 is a front view of a section of the patient-specific-bone-graft cage of FIG. 11.
Figure 14:
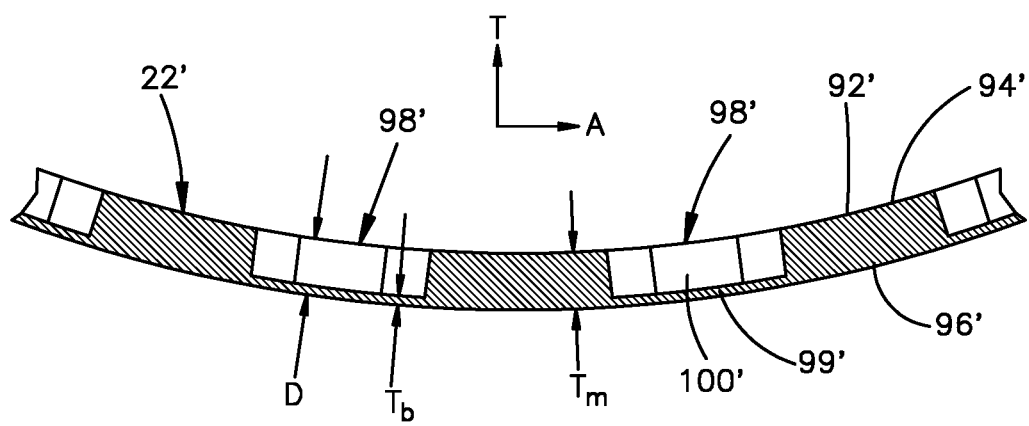
FIG. 14 is a cross-sectional view of the section of the patient-specific-bone-graft cage of FIG. 13.

Referring to FIGS. 13 and 14, the flexible membrane 22' may include a main body 92' that defines a front surface 94' (an example of a "first surface") and a back surface 96' (an example of a "second surface") that is opposite the front surface 94' along the transverse T direction.

The front surface 94' may define the inner surface 26' (see FIG. 10) and the back surface 96' may define the outer surface 28' (see FIG. 10). For example, the front surface 94' and the back surface 96' may be curved (e.g., in the transverse direction T along the lateral direction A and/or in the transverse direction T along the longitudinal direction L). The front surface 94' and the back surface 96' may together define the entire reconstructed anatomical structure including the reconstructed orbital roof 70' and the reconstructed lateral wall 76' (see FIG. 10).

The flexible membrane 22' may be flexible from an unflexed position to a flexed position. Flexing of the flexible membrane 22' may facilitate contouring and/or implantation of the flexible membrane 22'.

For example, the front surface 94' and the back surface 96' are illustrated as being curved in the transverse direction T. When in the curved position, the flexible membrane 22' may be transitioned to the flexed position such that the front surface 94' and the back surface 96' are curved more or curved less to conform to the contour of the replaced or reconstructed anatomical structure. In an embodiment, the front surface and the back surface are contoured to match or substantially match the contour of the of the replaced or reconstructed anatomical structure when in the unflexed position, and the flexible membrane may be transitioned to the flexed position.

The flexible membrane 22' may include a plurality of apertures 98' that are defined by the main body 92'. The apertures 98' may have a recessed depth D of 1.2 mm to 4.2 mm.

The main body 92' defines a base 99' of the apertures 98' that is disposed between the front surface 94' and the back surface 96'. For example, the apertures 98' may be open from the front surface 94' to the base 99' in the rearward direction. In an embodiment, at least some or all of the apertures are open at the front and the back, that is the apertures are through holes that extend through the front surface and the back surface of the main body.

The apertures 98' may have a hexagonal shape in a cross-sectional plane that is parallel to the base 99'. The shape and size of the apertures 98' may be substantially uniform along the depth D. In some embodiments, at least some of the apertures are tapered along the depth D. In another embodiment, some or all of the apertures have a different cross-sectional shape and/or size. For example, at least some of the apertures may have irregular hexagonal cross-sections, a larger cross-sectional size than adjacent apertures, and/or another irregular shape, which can enable the thickness of the walls to be substantially uniform between curved portions of the front surface and the back surface. In some embodiments, the cross-sectional shape of some or all of the apertures varies along the depth of the apertures.

Referring still to FIGS. 13 and 14, the apertures 98' may be separated from one another by at least one side wall 100' of the main body 92'. The side wall 100' may extend from the front surface 94' to the base 99'. The side wall can be curved, for instance, to define an oval, circular, or other curved shape of the aperture in the cross-sectional plane. Or the flexible membrane 22 may include a plurality of side walls 100' that combine to define a shape, such as a hexagon, a square, an octagon, a triangle, a rectangle, or any other regular or irregular geometric shape as desired, in the cross-sectional plane.

The side wall 100' may be a plurality of sidewalls 100' that define and uniformly separate each of the apertures 98' from one another. For example, each aperture 98' may be spaced from each adjacent aperture 98' by a wall width $W_w$ of 0.8 mm. In another embodiment, the wall width $W_w$ is substantially 0.8 mm. In some embodiments, the side wall is tapered along a direction extending from the back surface to the front surface.

Each of the side walls 100' may be straight and angled with respect to any adjacent connected side walls 100. For example, multiple adjacent side walls 100' combine to define the outer perimeters of a corresponding aperture 98'. These side walls 100' may form a hexagonal shape substantially perpendicular to the transverse direction T and/or parallel to a plane defined by the back surface 96'.

The main body 92' may have a thickness at the wall 100' that is equal to the total thickness $T_m$ of 2.0 mm to 5.0 mm. In another embodiment, the total thickness $T_m$ is about 2.0 mm to about 5.0 mm. The thickness $T_m$ may be constant along the length and width of each wall 100'. In some embodiments, the thickness $T_m$ is not constant along the length and/or width.

At the apertures 98', on the other hand, the thickness $T_b$ of the main body 92' may be significantly reduced. For example, the main body 92' has a thickness $T_b$ of 0.8 mm behind at least one of the apertures 98' of the plurality of apertures. The thickness $T_b$ may be constant along the length and width of each aperture 98'. In some embodiments, the thickness $T_b$ is not constant along the length and/or width.

The recessed depth D may be dependent upon the total thickness $T_m$ and the thickness $T_b$. For example, the recessed depth D may be 0.8 mm less than the total thickness $T_m$ in various embodiments. In an embodiment, the thickness $T_b$ is about 0.8 mm.

Although the disclosure has been described in detail, it should be understood that various changes, substitutions, and alterations can be made herein without departing from the spirit and scope of the invention as defined by the appended claims. Additionally, any of the embodiments disclosed herein can incorporate features disclosed with respect to any of the other embodiments disclosed herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A method of making a patient-specific bone graft cage computer model for forming a patient-specific bone graft cage to construct a portion of a defective mid-face region of a patient's skull, the method comprising:
    generating an initial-computer model of the patient's bone structure;
    extrapolating a surface of a bone in the defective mid-face region wherein the surface defines a void in the defective mid-face region, and wherein the extrapolating the surface step includes identifying a plurality of landmark locations around a periphery, of the surface, defining the void in the defective mid-face region to determine a contour of the surface; and
    generating the patient-specific bone graft cage computer model based on the initial-computer model and the extrapolation of the surface of the bone, wherein the patient-specific bone graft cage computer model is configured to match the extrapolation of the surface, wherein the patient-specific bone graft cage computer model is weakened by including a plurality of apertures that are configured to receive bone graft material such that each of the plurality of apertures includes an open end and terminates at a closed end opposite the open end, and wherein the open end is configured to receive the bone graft material, and the a closed end is defined by a base that is configured to support the bone graft material.

2. The method of claim 1, wherein the extrapolating the surface step includes:
    identifying a plurality of locations around the periphery of the surface defining the void in a defective orbital region to determine the contour of the surface.

3. The method of claim 1, wherein the extrapolating the surface step includes performing a statistical shape analysis, a Gaussian process, or a principal component analysis based on the contour of the surface of the bone defining the void in a defective orbital region.

4. The method of claim 1, wherein the generated patient-specific bone graft cage computer model is based on a statistical shape model, a Gaussian process model, or a principal component model.

5. The method of claim 1, further including:
    forming a patient-specific bone graft cage based on the patient-specific bone graft cage computer model such that the patient-specific bone graft cage is configured to contact the periphery of the surface of the bone when the patient-specific bone graft cage at least partially fills the void to construct the portion of the defective mid-face region.

6. The method of claim 5, wherein the forming a patient-specific bone graft cage step includes 3D printing the patient-specific bone graft cage.

7. The method of claim 5, wherein the patient-specific bone graft cage is formed as a single monolithic piece.

8. The method of claim 5, further including inserting bone graft material into the plurality of apertures of the patient-specific bone graft cage.

9. The method of claim 5 in combination with a method of using the patient-specific bone graft cage, comprising:
    implanting the patient-specific bone graft cage into the void in the defective mid-face region of the patient's skull.

10. The method of claim 9, wherein the patient-specific bone graft cage is fixed in the defective mid-face region without a fastener.

11. The method of claim 1, wherein the generating the initial-mirrored-computer model step includes generating an initial-mirrored-computer model of the patient's bone structure by mirroring a 3D image of a healthy and undamaged orbital region, and wherein the generating the patient-specific bone graft cage computer model is based on the initial-mirrored-computer model.

12. The method of claim 1, wherein the defective mid-face region is a defective orbital region.

* * * * *